(12) United States Patent
Von Wallfeld et al.

(10) Patent No.: US 6,241,356 B1
(45) Date of Patent: Jun. 5, 2001

(54) METHOD FOR DETERMINING DATA FOR TREATING A SURFACE

(75) Inventors: Herbert Von Wallfeld, Julich; Thomas Neuhann, Müchen, both of (DE)

(73) Assignee: Technomed Gesellschaft für Med und Med.-Techn. Systeme mbH, Baesweiler (DE)

( * ) Notice: Subject to any disclaimer, the term of this patent is extended or adjusted under 35 U.S.C. 154(b) by 0 days.

(21) Appl. No.: 09/399,861

(22) Filed: Sep. 21, 1999

Related U.S. Application Data

(63) Continuation of application No. PCT/DE98/00426, filed on Feb. 14, 1998.

(30) Foreign Application Priority Data

Mar. 25, 1997 (DE) ............................................... 197 12 328
Apr. 2, 1997 (DE) ............................................... 197 13 623

(51) Int. Cl.⁷ ....................................................... A61B 3/10
(52) U.S. Cl. ............................................................ 351/212
(58) Field of Search .................................. 351/205, 211, 351/212, 246, 247; 600/437, 443; 606/166, 5, 4

(56) References Cited

U.S. PATENT DOCUMENTS

| | | |
|---|---|---|
| 4,669,466 | 6/1987 | L'Esperance . |
| 5,384,608 | 1/1995 | Gersten . |
| 5,989,189 * | 11/1999 | LeBlanc et al. ................. 600/437 |

FOREIGN PATENT DOCUMENTS

| | | |
|---|---|---|
| 36 07 721 A1 | 9/1987 | (DE) . |
| 38 33 715 A1 | 5/1989 | (DE) . |
| 40 06 949 A1 | 9/1991 | (DE) . |
| 43 05 842 A1 | 9/1994 | (DE) . |
| 195 22 915 A1 | 1/1996 | (DE) . |
| 195 01 069 A1 | 7/1996 | (DE) . |
| WO 98/08048 | 2/1998 | (WO) . |

OTHER PUBLICATIONS

Gehring Georg et al.: Schneller vom Modell zum Produkt bei Freiformaflächen. In: Werkstatt und Betrieb, 128, 1995, No. 11, p. 977–982.

Digitale Freiformlehre—ein Werkzeug zum wirtschaftlichen Messen und Digitalisieren von Freiformflächen. In: fertigung, Jan. 1993, p. 26–30.

Firmenschrift of FA. Zeiss, Oberkochen, Messdatenqualität in neuer Dimension, 60–20–081–D, Oct. 4, 1994.

Koordinationsmesstechnik in "Die Bibliothek der Technik 41", Verlag moderne industrie AG & Co., Landsberg/Lech, p. 45–51, fig. 44.

* cited by examiner

*Primary Examiner*—George Manuel
(74) *Attorney, Agent, or Firm*—Henry M. Feiereisen; Ursula B. Day

(57) ABSTRACT

A method for determining data for adapting a reflective surface to a desired surface, includes the steps of determining spatial co-ordinates of a multiple number of points of a surface and entering the determined spatial co-ordinates into a computer as a data record. Recorded in the computer are then shape and/or position of a desired surface, with the shape and/or position of the desired surface being variable. The computer calculates for the multiple number of points on the surface the spacing to the desired surface. The spatial co-ordinates and spacings of the multiple number of points are then outputted as a data record for adjusting the surface. By simulating the treatment process on the computer in advance, it is possible to select the optimal treatment process and to eliminate regional unevenness on the cornea.

9 Claims, 1 Drawing Sheet

METHOD FOR DETERMINING DATA FOR TREATING A SURFACE

CROSS-REFERENCES TO RELATED APPLICATIONS

This application is a continuation of prior filed copending PCT International application no. PCT/DE98/00426, filed Feb. 14, 1998.

BACKGROUND OF THE INVENTION

The invention concerns a method for determining data for treating a surface, and in particular to a method for adapting a reflective surface to a desired surface.

When treating the cornea of an eye, usually the refractive behavior of the cornea is determined in order to subsequently, in most cases by means of a laser method, subject the cornea to laser treatment so as to change the curvature and thus the refractive behavior of the cornea. In thus it is possible, by means of subjecting the cornea to a few targeted "exposures", to achieve a structural change of the cornea in certain regions of the remove parts of the cornea. In particular by radially different intensity of the laser treatment, the refractive behavior of the surface of the cornea is thus changed.

It has however been shown that usually the refractive behavior of the cornea is not uniform across its entire surface and consequently the known procedures produce a good result only in the case of refractive behavior distributed at adequate similarity across the cornea. With the known treatment methods, smaller areas of the cornea of particularly high or particularly low curvature are not corrected at all or only inadequately corrected.

U.S. Pat. Nos. 4,669,466 and 5,384,608 describe methods in which spatial co-ordinates of a multiple number of points on a surface are determined and entered as a data record in a computer in which also the form and shape of a desired surface is recorded. For the multiple number of points on the surface, the spacing to the desired surface is calculated, and the spatial co-ordinates and the spacings of the multiple number of points is outputted as a data record for adapting the surface.

These known methods determine a desired surface and try to treat the surface in such a way as to eliminate the differences to the desired surface. It is however problematic that for a surface of any given form, it is impossible to unambiguously determine a desired surface. An optimal desired surface can only be determined if the spacings to the surface are known.

SUMMARY OF THE INVENTION

It is thus an object of the present invention to provide an improved method for determining data for treating a surface, in particular a cornea, obviating the afore-stated drawbacks.

In particular, it is an object of the invention to propose an improved method for determining data for treating a surface, in particular a cornea, which method makes it possible, by treating locations of various curvature on a surface such as for example a cornea, to reduce such locations.

It is still another object of the present invention to provide an improved method to reduce locations of the most varied curvature on a surface, using minimal intervention, in order to achieve a surface curvature suitable for the individual case.

These objects, and others which will become apparent hereinafter, are attained in accordance with the present invention by determining the locations of a multiple number of points on the surface; entering these locations into a computer as a date record; entering the form and/or shape of a desired surface into the computer, with the shape and/or position of the desired surface being variable; calculating for the multiple number of points on the surface, the spacing to the desired surface; and outputting location and spacing of the multiple number of points as a data record for treating the surface.

The method according to the present invention is based on the recognition that for a surface of any given form, it is impossible to unambiguously determine a desired surface. Only by repeated changing of the desired surface and respective determination of the necessary steps, is the surgeon in a position to determine a desired surface which serves as a basis for further treatment.

The method according to the invention makes it possible not only to treat the surface as a whole but depending on the resolution, to determine the position of each individual point on the cornea in order to subsequently, by comparison with a predetermined desired surface, calculate the positive or negative spacing to the desired surface, and make it available for the actual treatment of the surface. In this way, local regional peaks can be treated more intensively while naturally existing troughs are treated to a lesser extent or not treated at all. The data record made available by the method thus makes possible a targeted treatment of even a relatively uneven cornea which is to comprise a regular curvature across its entire area as a result of the subsequent treatment method.

Since the form and/or position of the desired surface is variable, it is possible to determine the desired surface on the computer in comparison with the surface of the cornea on the basis of clinical experience. Deviations between the desired surface and the cornea, which is calculated in an instant by the computer, assist the surgeon in correctly determining the desired surface.

The method is above all suitable for reflective surfaces because these can be measured easily by means of topometry.

A simple method for determining the locations of a multiple number of points on the surface consists of computing the locations of the surface of the multiple number of points topometrically in an iterative manner, as co-ordinates. An iterative method of computing the co-ordinates of individual locations on a reflective surface is described in PCT/DE95/01579, the full extent of which is referred to herewith.

To facilitate work to the treating surgeon, it is advantageous if the locations of the multiple number of points are graphically represented. To do so, e.g. a grid representation is suitable which clearly shows the progression of the corneal shape or the deviation of the shape from a spherical surface.

For better comparison it is advantageous if the shape and/or position of the desired surface too are/is graphically represented. To this effect the same methods can be used, with the surfaces to be represented either side-by side or in their relative arrangements to each other.

A further embodiment of the invention provides for the spacings between the multiple number of points and the desired surface, too, to be graphically represented. This too can be made available to the treating surgeon as graphics in three-dimensional representations, projections or sectional representations.

Particularly easy comprehension of the representation is achieved in that various spacings are represented by different colors. This makes it possible for the treating surgeon to recognize the areas of particularly extensive deviation from the desired curve, without necessitating expensive numeric comparison.

As an alternative, or as a supplement to determining the desired surface according to clinical experience, the desired surface can also be determined by ray tracing. In this, a desired curve for the cornea is calculated on the basis of certain requirements of the course of the beams and in particular their intersection with the retina.

A further embodiment of the invention provides for simulation of a surface treatment provides for simulation of a surface treatment method with the data record, for treating the surface and for the result to be displayed. To this effect additionally, the data for a special surface treatment method is entered, after which the computer displays the result achievable with this surface treatment method to the treating surgeon.

If the surface treatment method is for example a laser treatment method, then the data of the change in shape of the cornea caused by a single exposure can be entered into the computer. The computer then calculates the location and number of the necessary exposures for approximating the surface of the cornea to the desired surface. If the result ins not satisfactory, either the surface treatment method can be changed, or the location or course of the desired surface I varied. The computer makes it possible within an instant to simulate various treatment methods and desired surface inputs right up to displaying the achievable result, so as to carry out the optimum treatment method on the patient.

BRIEF DESCRIPTION OF THE DRAWING

The above and other objects, features and advantages of the present invention will now be described in more detail with reference to the accompanying drawing, in which.

DETAILED DESCRIPTION OF PREFERRED EMBODIMENTS

Figure 1:
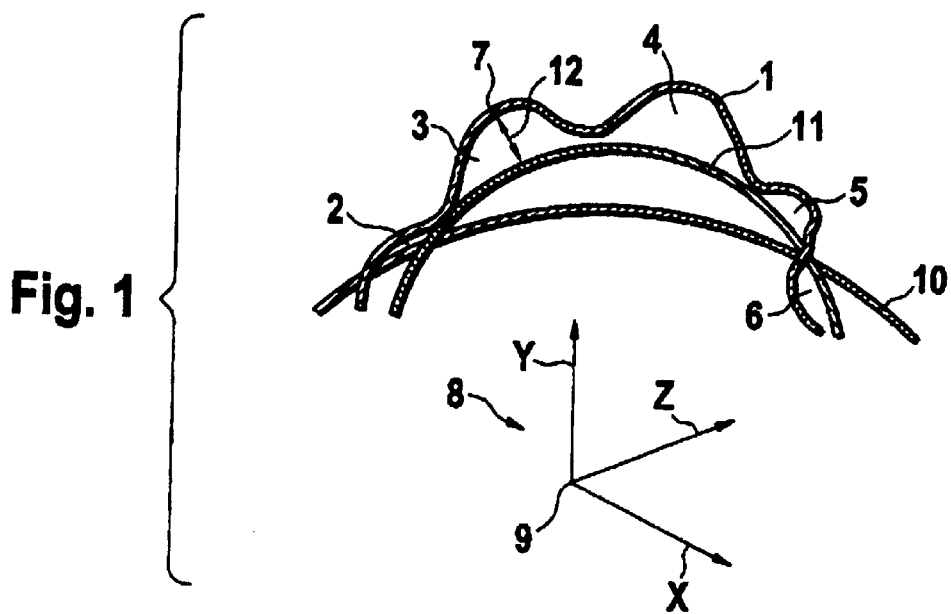
FIG. 1 is a sectional view of a cornea with exaggerated surface deformation.

Throughout all the Figures, same or corresponding elements are generally indicated by same reference numerals.

Turning now to the drawing, and in particular to FIG. 1, there is shown a sectional view of a cornea with exaggerated surface deformation. The surface of the cornea 1 is shown with highly exaggerated irregularities 2, 3, 4, 5 and 6. As an example of the multiple number of points, point 7 is shown, the location of which can be determined by means of the co-ordinates of a co-ordinate system 8 with the randomly determined zero point 9. Thus for each point on the cornea 1 there is a co-ordinate reference which exactly determines the location of the point.

In addition, in FIG. 1 a first desired surface 10 has been drawn in which can be varied to such an extent by the treating surgeon that the location and course match the clinical requirements. The variation gives rise to a second desired surface 11 which is positioned relative to the cornea by the surgeon according to his clinical experience.

From the relative position of each pint 7 to the second desired surface 11, the computer calculates the spacing 12 for each individual point. This spacing serves as a basis for the subsequent treatment of the cornea 1.

Figure 2:
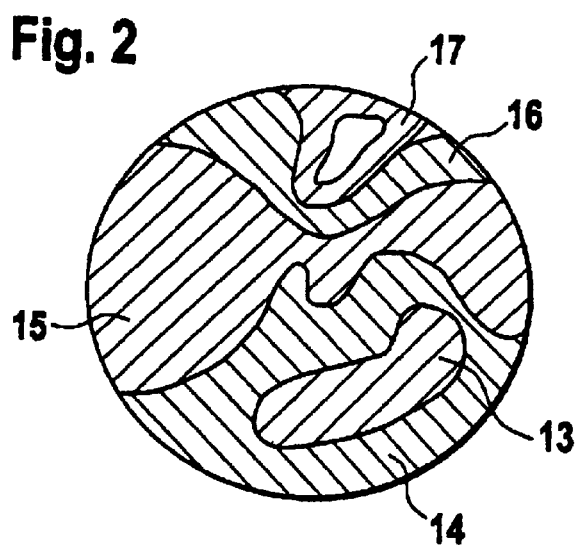
FIG. 2 is a top view of a cornea with its varying curvature areas.

FIG. 2 is a top view showing possible curvatures of a cornea, represented by different hatching or crosshatching. Tight hatching 13, 14, 15 indicates a stronger curvature while lighter hatching 16, 17 indicates a lesser curvature. Instead of hatching, the use of colors is advantageous in practical application.

As an alternative to, or supplement to the curvatures, it is also possible to represent the locations of the surface of the cornea.

The spacings 12 between the cornea 1 and the second desired surface 11 can also be represented analogously to FIG. 2 by hatching or colors, so as to highlight areas which require particularly strong treatment.

Figure 3:
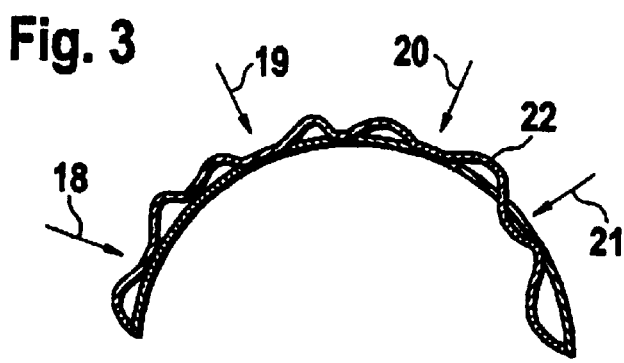
FIG. 3 is a sectional view of the cornea according to FIG. 1 after laser treatment.

FIG. 3 is a diagrammatic representation of treatment of the surface of a cornea according to FIG. 1 using a laser device. Based on the spacings between the cornea 1 and the second desired surface 11, the computer calculated the location and number of the exposures 18, 19, 20, 21. However, since the laser device only allows discontinuous settings, after treatment an actual surface 18 results which only approximates the second desired surface 11. At first the treatment is simulated on the computer to verify the result expected from carrying out treatment and if necessary for adjustment of the treatment method. Only after playing through various desired surfaces and or treatment methods does the treating surgeon finally determine a desired surface and a surface treatment method which most closely meet the intended result.

While the invention has been illustrated and described as embodied in a method for determining data for treating a surface, it is not intended to be limited to the details shown since various modifications and structural changes may be made without departing in any way from the spirit of the present invention.

What is claimed as new and desired to be protected by letters patent is set forth in the appended claims:

What is claimed is:

1. A method to determine data for adapting a reflective surface to a desired surface, comprising the steps of:

determining spatial co-ordinates of a multiple number of points of a surface;

entering the determined spatial co-ordinates into a computer as a data record;

entering at least one of shape and position of a desired surface into the computer;

calculating for the multiple number of points on the surface the spacing to the desired surface; and outputting the spatial co-ordinates and spacings of the multiple number of points as a data record for adjusting the surface, wherein at least the one of the shape and position of the desired surface is variable.

2. The method of claim 1, wherein the surface is a reflective surface which is being measured by means of topometry.

3. The method of claim 1, wherein the surface is a cornea.

4. The method of claim 1, wherein the spatial co-ordinates of the surface of the multiple number of points are iteratively calculated.

5. The method of claim 1, wherein the spacings between the multiple number of points and the desired surface are represented graphically.

6. The method of claim 1, wherein the spacings are represented by different colors.

7. The method of claim 1, wherein the at least one of the shape and position of the desired surface is determined by ray tracing.

8. The method of claim 1, wherein with the data record for adapting the surface a surface treatment method is simulated and the result is displayed.

9. The method of claim 8, wherein the surface treatment method is a laser method.

* * * * *